United States Patent
Kuhara et al.

(10) Patent No.: US 9,532,728 B2
(45) Date of Patent: Jan. 3, 2017

(54) MAGNETIC RESONANCE IMAGING APPARATUS

(75) Inventors: Shigehide Kuhara, Otawara (JP); Ayako Ninomiya, Tokyo (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1301 days.

(21) Appl. No.: 13/010,042

(22) Filed: Jan. 20, 2011

(65) Prior Publication Data

US 2011/0178388 A1    Jul. 21, 2011

(30) Foreign Application Priority Data

Jan. 20, 2010  (JP) ................................ 2010-010413

(51) Int. Cl.
| | |
|---|---|
| *A61B 5/00* | (2006.01) |
| *A61B 5/055* | (2006.01) |
| *A61B 5/113* | (2006.01) |
| *A61B 5/0456* | (2006.01) |

(52) U.S. Cl.
CPC .............. *A61B 5/055* (2013.01); *A61B 5/0037* (2013.01); *A61B 5/0044* (2013.01); *A61B 5/0456* (2013.01); *A61B 5/113* (2013.01); *A61B 5/1135* (2013.01); *A61B 5/7292* (2013.01)

(58) Field of Classification Search
CPC ..... A61B 5/055; A61B 5/0456; A61B 5/7292; A61B 5/1135
See application file for complete search history.

(56) References Cited

U.S. PATENT DOCUMENTS

| | | | | |
|---|---|---|---|---|
| 6,070,097 A | * | 5/2000 | Kreger ................. | A61B 5/0456 600/413 |
| 6,292,683 B1 | * | 9/2001 | Gupta .................. | G06T 3/0075 324/307 |
| 7,432,710 B2 | | 10/2008 | Takei et al. | |
| 2007/0088212 A1 | * | 4/2007 | Takei ..................... | A61B 5/055 600/413 |
| 2008/0200800 A1 | | 8/2008 | Kuhara | |
| 2008/0226149 A1 | * | 9/2008 | Wischmann .......... | A61B 6/503 382/131 |

(Continued)

FOREIGN PATENT DOCUMENTS

| | | |
|---|---|---|
| CN | 1432341 | 7/2003 |
| CN | 1943510 | 4/2007 |

(Continued)

OTHER PUBLICATIONS

Carlson, et al., "Intermittent Mode CT Fluoroscopy-guided Biopsy of the Lung or Upper Abdomen with Breath-hold Monitoring and Feedback: System Development and Feasibility," *Radiology*, vol. 229, pp. 906-912 (2003).

(Continued)

*Primary Examiner* — Rajeev Siripurapu
(74) *Attorney, Agent, or Firm* — Nixon & Vanderhye P.C.

(57) ABSTRACT

An image processing apparatus stores data for a series of images associated with a range including a heart and diaphragm of an object. A temporal change in a moving amount of the diaphragm and a temporal change in a moving amount of the heart are generated from the series of images, and a ratio of (a) the moving amount of the heart to (b) the moving amount of the diaphragm is calculated.

19 Claims, 8 Drawing Sheets

(56) References Cited

U.S. PATENT DOCUMENTS

2008/0231271 A1* 9/2008 Yui et al. ...................... 324/307
2008/0281186 A1 11/2008 Kuhara

FOREIGN PATENT DOCUMENTS

| | | |
|---|---|---|
| CN | 1951323 | 4/2007 |
| JP | 2000-41970 | 2/2000 |
| JP | 2000-157507 | 6/2000 |
| JP | 2002-28150 | 1/2002 |
| JP | 2004-57226 | 2/2004 |
| JP | 2005-278919 | 10/2005 |
| JP | 2006-26076 | 2/2006 |
| JP | 2007-29250 | 2/2007 |
| JP | 2007-229443 | 9/2007 |
| JP | 2008-148806 | 7/2008 |
| JP | 2008-302214 | 12/2008 |
| JP | 2009-178264 | 8/2009 |

OTHER PUBLICATIONS

Chinese Office Action mailed Feb. 5, 2010, in CN 2008-10095660.7, including English translation.
Chinese Office Action mailed Apr. 18, 2011, in CN 2009-10206344,7, including English translation.
Chinese Office Action mailed Dec. 11, 2011, in CN 2010-10260781.X, including English translation.
JP Office Action in JP 2010-010413 mailed Nov. 26, 2013 with English translation.

* cited by examiner

MAGNETIC RESONANCE IMAGING APPARATUS

CROSS-REFERENCE TO RELATED APPLICATIONS

This application is based upon and claims the benefit of priority from Japanese Patent Application No. 2010-010413, filed Jan. 20, 2010; the entire contents of which are incorporated herein by reference.

FIELD

Embodiments described herein relate generally to a magnetic resonance imaging apparatus.

BACKGROUND

When a magnetic resonance imaging apparatus captures an image of coronary arteries, in particular an image of the coronary artery distribution of the whole heart (Whole Heart MRCA), the apparatus uses a method of imaging under natural aspiration using a 3D ssfp (steady state free precession) sequence. At this time, the apparatus performs imaging while correcting the movement of the heart due to respiratory movement by using the RMC (Real-time Motion Correction) method. The RMC method detects the position of the diaphragm by using an NMR signal, and corrects respiratory movement while moving the imaging slab position of a heart portion in real time based on the detected information, thereby performing imaging.

In practice, however, there are variations between the moving amount of the diaphragm and the moving amount of the heart. The variations also change in accordance with respiratory phases, and also differ among individuals with different physiques and the like. It is therefore impossible to specify such variations as eigenvalues. This makes it very difficult to prevent a deterioration in image quality.

DETAILED DESCRIPTION

In general, according to one embodiment, a magnetic resonance imaging apparatus repeats an imaging scan on the overall heart of an object, detects the moving amount of the diaphragm due the respiratory movement of the object by executing a probe scan immediately before each of the imaging scans, and moves an imaging range by each of the imaging scans based on the detected moving amount of the diaphragm. This magnetic resonance imaging apparatus includes a control unit configured to control an RF coil transmission/reception unit and a gradient field power supply to repeatedly capture data of at least one image associated with at least one slice including the heart and the diaphragm by ECG gating as a preliminary scan for the probe scan and the imaging scan. A moving amount generating unit generates a temporal change in moving amount of the diaphragm and a temporal change in moving amount of the heart from the repeatedly captured images. A ratio calculation unit calculates the ratio of the moving amount of the heart to the moving amount of the diaphragm based on the temporal change in moving amount of the diaphragm and the temporal change in moving amount of the heart. An imaging range moving amount calculation unit calculates the moving amount of an imaging range by each of the imaging scans upon correcting the moving amount of the diaphragm by each of the probe scans based on the calculated ratio.

This embodiment will be described below with reference to the views of the accompanying drawing.

Figure 1:
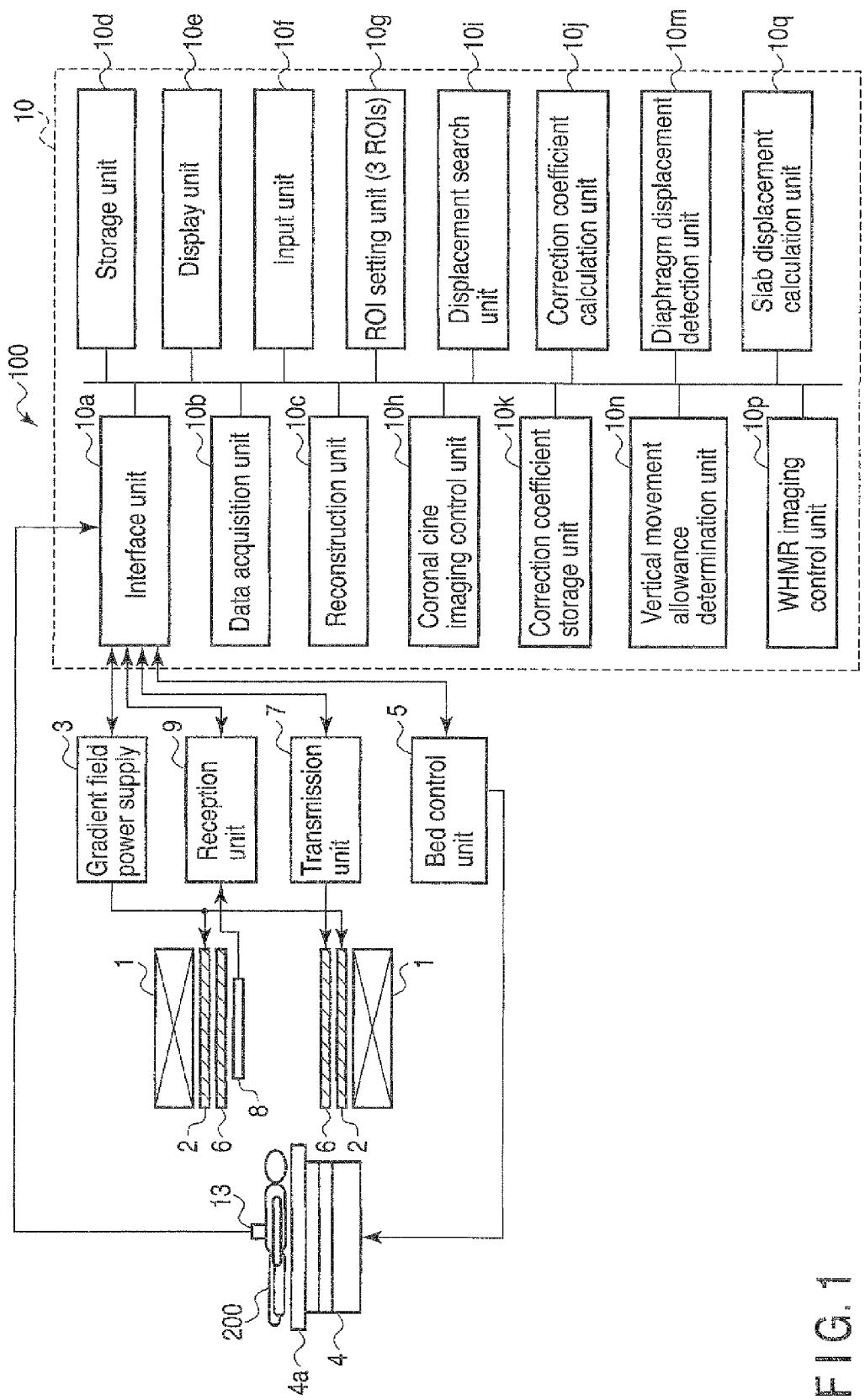
FIG. 1 is a block diagram showing the arrangement of a magnetic resonance imaging apparatus according to this embodiment.

FIG. 1 shows the arrangement of a magnetic resonance imaging apparatus (MRI apparatus) according to this embodiment. An MRI apparatus 100 includes control computer circuits 10 connected to control MRI gantry components 1-9. The static field magnet 1 typically has a hollow cylindrical shape. The static field magnet 1 generates a uniform static field in the cylindrical portion. The static field magnet 1 is formed by a permanent magnet or superconductive magnet.

A gradient field coil unit 2 is placed inside the static field magnet 1. The gradient field coil unit 2 includes a combination of three types of coils, i.e., X-, Y-, and Z-axis coils, respectively corresponding to the orthogonal X-, Y-, and Z-axes. The Z-axis is defined on the cylindrical centerline. The body axis of an object inserted in the cylindrical space almost coincides with the Z-axis. The X- and Y-axes are respectively defined in the horizontal and vertical directions. The three types of coils respectively receive currents supplied from a gradient field power supply 3 and generate gradient fields which change along the X-, Y-, and Z-axes. Note that a static field is formed parallel to the Z-axis. For example, the gradient fields along the X-, Y-, and Z-axes are respectively and arbitrarily used as a slice selecting gradient field Gs, a phase encoding gradient field Ge, and a readout gradient field Gr. The slice selecting gradient field Gs is used to arbitrarily determine an imaging slice. The phase encoding gradient field Ge is used to change the phase of an NMR signal in accordance with a spatial position. The readout gradient field Gr is used to change the frequency of an NMR signal in accordance with a spatial position.

A bed 4 includes a top 4a movable in the Z-axis direction. An object 200 is inserted into the cylindrical space of the gradient field coil unit 2 while being placed on the top 4a. A bed control unit 5 controls the movement of the top 4a. An electrocardiograph (ECG) 13 is attached to the object 200.

A transmission RF coil 6 is placed inside the gradient field coil unit 2. The transmission RF coil 6 receives high-frequency pulses from a transmission unit 7 and generates a high-frequency magnetic field. The transmission unit 7 transmits high-frequency pulses corresponding to the Larmor frequency to the transmission RF coil 6. A reception RF coil 8 is placed inside the gradient field coil unit 2. The reception RE coil 8 receives the NMR signal emitted from the object due to the influence of the above high-frequency magnetic field. A reception unit 9 receives an output signal from the reception RF coil 8. The reception unit 9 generates NMR signal data based on the output signal from the reception RF coil 8.

A control computer system 10 is connected to the gradient field power supply 3, the bed control unit 5, the transmission unit 7, the reception unit 9, and the ECG 13 via an interface unit 10a. A data acquisition unit 10b acquires via the interface unit 10a the digital signals output from the reception unit 9. The data acquisition unit 10b stores the acquired digital signal, i.e., the NMR signal data, in a storage unit 10d. A reconstruction unit 10c executes reconstruction processing such as Fourier transformation based on the NMR signal data stored in the storage unit 10d. This generates the spectrum data or image data of a desired nuclear spin in the object 200. The storage unit 10d stores NMR signal data and spectrum data or image data for each patient.

A display unit 10e is provided to display various kinds of information such as spectrum data and image data. An input unit 10f is provided to allow the operator to input various kinds of commands and information to the computer system 10. It is possible to use, as the input unit 10f, pointing devices such as a mouse and a trackball, selection devices such as a mode switch, and input devices such as a keyboard, as needed. For example, the operator inputs via the input unit 10f a region (slab) for imaging the overall heart, a region (motion probe) for detecting the position of the diaphragm, and a region (ROI) for detecting the position of the heart.

This embodiment uses a technique called RMC (Real-time Motion Correction) to suitably image the overall heart of an object while tracking the overall heart which moves due to the respiratory movement of the object. In RMC, this apparatus repeats an imaging scan (slab scan) accompanying phase-encode increment using a two- or three-dimensional Fourier transform method. Immediately before each imaging scan, the apparatus executes a probe scan (navigator scan) for detecting the moving distance, i.e., the moving amount, of the diaphragm, which moves due to the respiratory movement of the object, from a reference position (the position in the first scan). The apparatus then moves the imaging range (excitation range) aiming at the overall heart by an imaging scan based on the moving amount of the diaphragm which is detected by each probe scan.

That is, in RMC, the moving amount of the heart is estimated based on the moving amount of the diaphragm. If there is a difference between the moving amount of the diaphragm and the moving amount of the heart, a deterioration in image quality occurs. Before the execution of a main scan (a probe scan and an imaging scan), this embodiment performs a preliminary scan to measure a correction coefficient for correcting the difference between the moving amount of the diaphragm and the moving amount of the heart. The embodiment executes a preliminary scan under the control of a coronal cine imaging control unit 10h.

Figure 2:
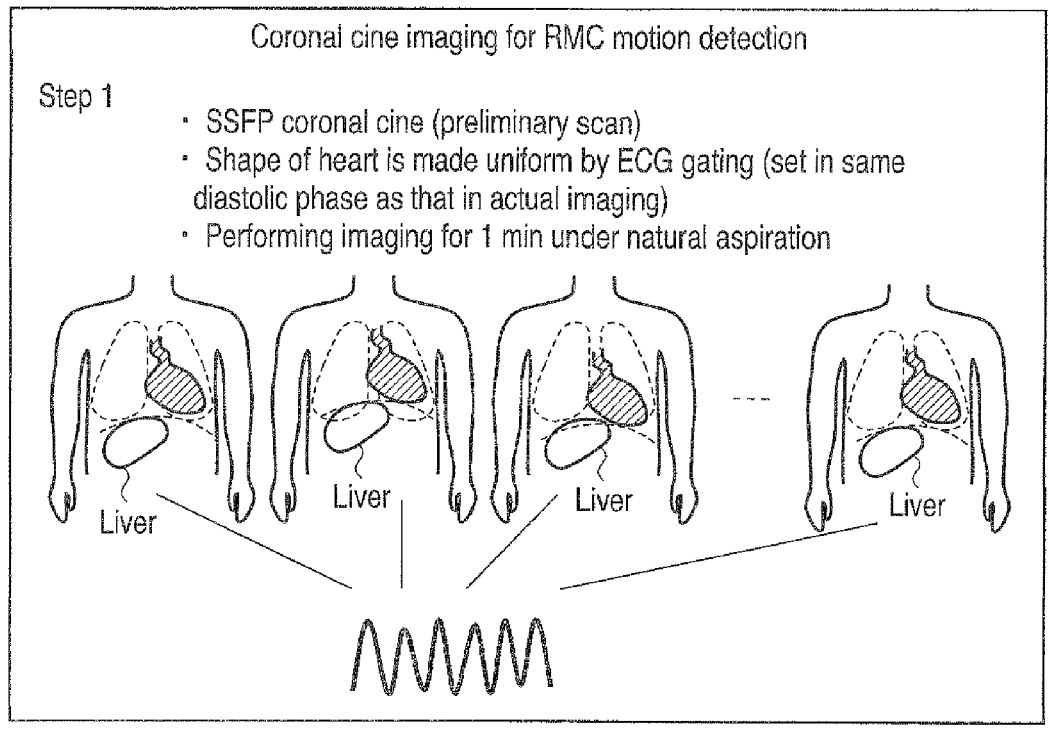
FIG. 2 is a view for explaining preliminary scanning (coronal cine imaging) according to this embodiment.

As shown in FIG. 2, the coronal cine imaging control unit 10h controls the transmission unit 7, the reception unit 9, and the gradient field power supply 3 to repeatedly capture a two-dimensional slice image, typically a coronal image, associated with a slice range including the overall heart and diaphragm of the object by ECG gating, and stores the images in the storage unit 10d. A preliminary scan uses the ssfp (steady state free precession) imaging method which applies gradient fields in directions opposite to those of the gradient fields Ge, Gs, and Gr so as to match transverse magnetization phases for each of repetitive excitations.

Cardiac phases corresponding to a series of coronal images (to be referred to as coronal cine images hereinafter) consecutively captured by ECG gating are set to be uniform. This cardiac phase is typically set to coincide with the coronary artery rest period (the systolic phase or diastolic phase) in which imaging is performed by a main scan (WHMRCA). An imaging scan for a coronal image is repeated for, for example, about 1 min under natural aspiration. An imaging slice for a coronal image is set to an oblique slice passing through the diaphragm on which a motion probe is placed in a navigator scan of a main scan and a portion near the center of the heart to be imaged. When imaging is to be performed at the apex, an imaging slice is set to a slice passing through the apex and the center of the heart.

Figure 13:
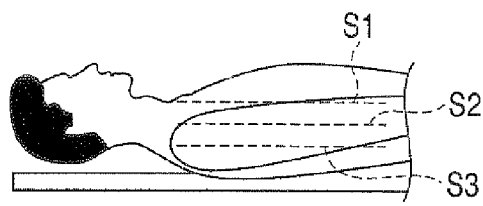
FIG. 13 is a view showing slices respectively set for three types of ROIs set by the ROI setting unit in FIG. 1.

A slice image is not limited to one slice. As shown in FIG. 13, it is possible to image a slice S1 traversing a diaphragm portion, a slice S2 traversing an upper cardiac portion, and a slice S3 traversing a lower cardiac portion. Although the place where a motion is detected differs from the place where the probe is placed, it is possible to perform imaging by using a sagittal slice and a coronal slice and perform conversion afterward.

Figure 3:
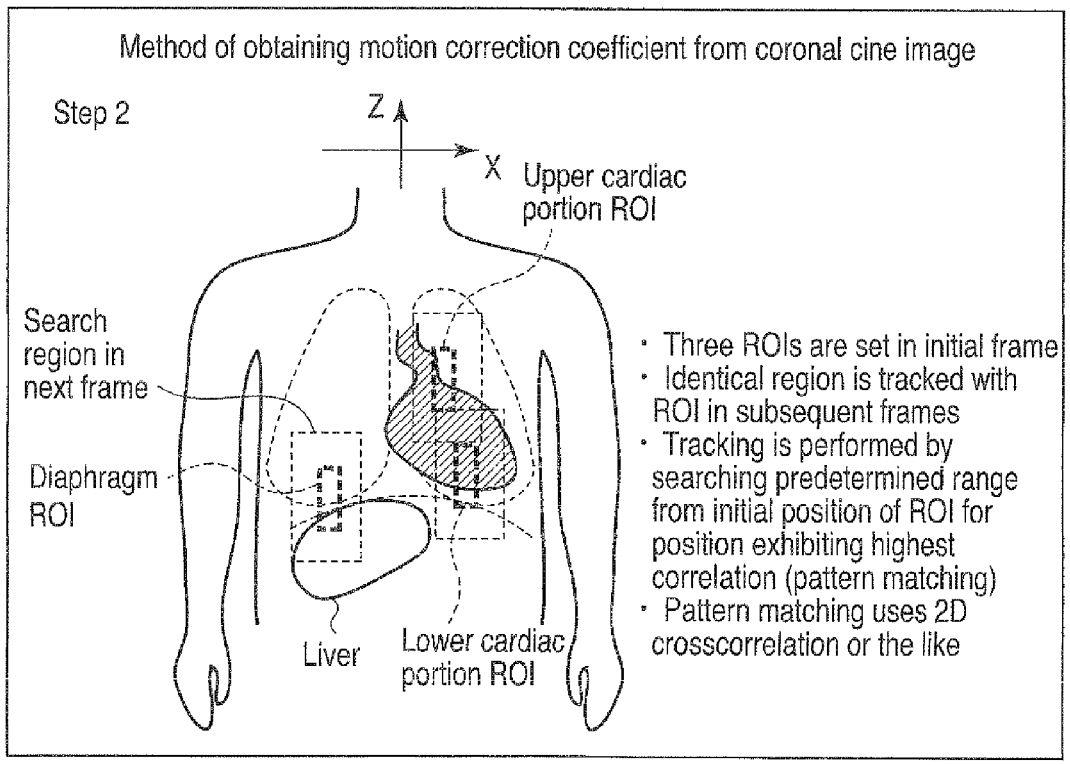
FIG. 3 is a view showing three types of ROIs set by an ROI setting unit in FIG. 1 and the corresponding search ranges.

After a preliminary scan, the apparatus obtains a correction coefficient by using a coronal cine image in a period before the start of a main scan. As shown in FIG. 3, the operator sets a diaphragm ROI at the position of the diaphragm, an upper portion ROI at the upper portion (Upper) of the heart, and a lower portion ROI at the lower portion (Lower) of the heart on a coronal image of the initial frame of a coronal cine image. The display unit 10e displays a coronal image of the initial frame. An ROI setting unit 10g sets a diagnosis ROI, an upper cardiac portion ROI, and a lower cardiac portion ROT in accordance with the operation of the input unit 10f by the operator. The operator sets a two-dimensional local region, typically a rectangular region having a longer side in the Z-axis direction parallel to the moving direction of the heart and diaphragm due to respiratory movement, in addition to the diaphragm ROI, the upper cardiac portion ROI, and the lower cardiac portion ROI. A diaphragm ROI is set to traverse the diaphragm. An upper cardiac portion ROI is set to traverse, for example, a marginal portion of the upper cardiac portion immediately below the pulmonary artery. A lower cardiac portion ROI is set to traverse a marginal portion of the lower cardiac portion. In addition, the ROI setting unit 10g sets search ranges, each representing a range for searching for the position at which the highest correlation coefficient is obtained in pattern matching, around the diaphragm ROI, the upper cardiac portion ROI, and the lower cardiac portion ROI so as to be centered on them. The search ranges are set to sizes and shapes obtained by enlarging, for example, the initially set diaphragm ROI, upper cardiac portion ROI, and lower cardiac portion ROI at predetermined ratios in the two directions, i.e., the X- and Z-axis directions. Note that the operator can properly select an initial frame.

Figure 4:
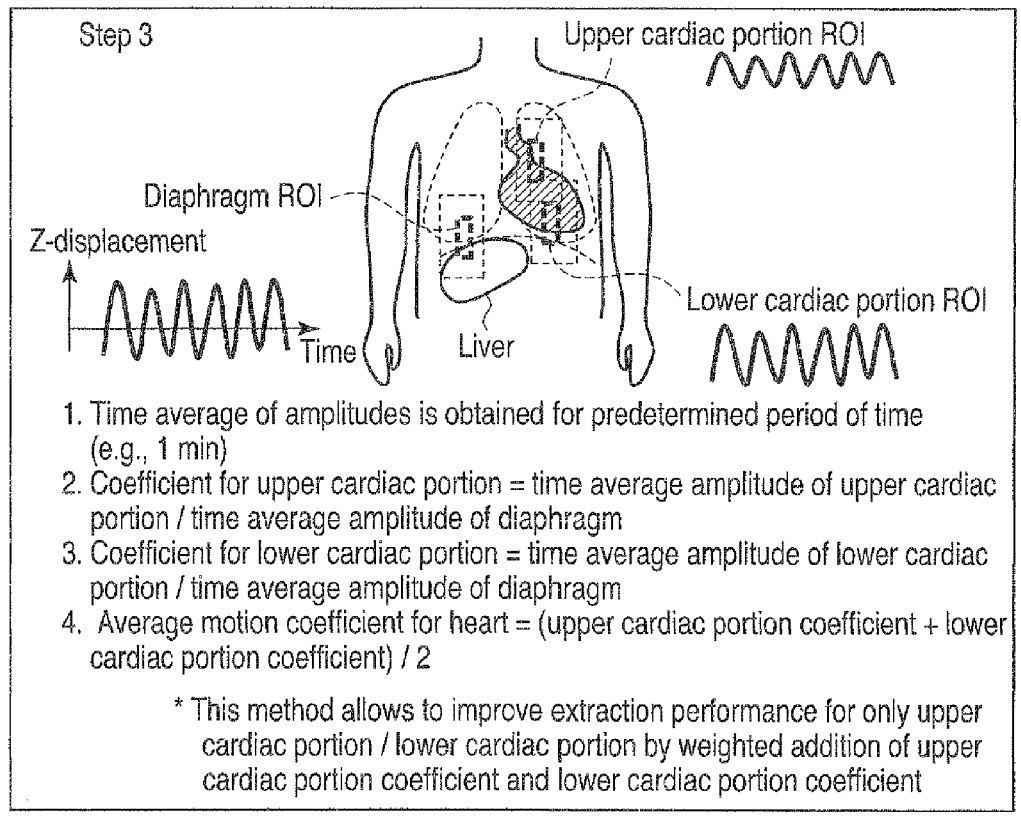
FIG. 4 is a view showing a method of calculating correction coefficients by a correction coefficient calculation unit in FIG. 1.

When the ROI setting unit 10g sets three ROIs, namely a diaphragm ROI, upper cardiac portion ROI, and lower cardiac portion ROI, on the initial frame, a displacement search unit 10i identifies, on each coronal image of the subsequent frames, the position of an ROI having a two-dimensional pixel pattern exhibiting the highest correlation coefficient, in each search range, relative to the two-dimensional pixel pattern (reference pattern) of the ROT (initial ROI) on each initial frame. The distance between each initial ROI and the corresponding identified ROI is obtained as a moving amount. The displacement search unit 10i measures the moving amounts of the three ROIs, namely the diaphragm ROI, upper cardiac portion ROI, and lower cardiac portion ROI, for each frame, thereby generating temporal changes in moving amount from the reference positions (initial ROIs), as shown in FIG. 4. Pattern matching uses two-dimensional crosscorrelation processing or the like. In this case, moving amounts are obtained as distances in the Z-axis direction. It is, however, possible to obtain moving amounts in two directions, namely the Z- and X-axis directions.

A correction coefficient calculation unit 10j then obtains a correction coefficient for correcting the difference between the moving amount of the diaphragm and the moving amount of the heart from measured temporal changes in the moving amount of the diaphragm, measured temporal changes in the moving amount of the upper cardiac portion, and temporal changes in the moving amount of the lower cardiac portion. This method will be described below with reference to FIG. 4. The following is a procedure for the method:

1) obtaining a predetermined time, e.g., the time average of amplitudes (moving amounts) for 1 min, from each of temporal changes in the moving amount of the diaphragm, temporal changes in the moving amount of the upper cardiac portion, and temporal changes in the moving amount of the lower cardiac portion;

2) upper cardiac portion correction coefficient=time average amplitude of upper cardiac portion/time average amplitude of diaphragm;

3) lower cardiac portion correction coefficient=time average amplitude or lower cardiac portion/time average amplitude of diaphragm; and 4) correction coefficient for overall heart=(upper cardiac portion coefficient+lower cardiac portion coefficient)/2.

A correction coefficient storage unit 10k stores the calculated correction coefficients to be used to correct the moving amount of the diaphragm into the moving amount of the heart in a main scan.

Note that the above method obtains a correction coefficient for the upper cardiac portion relative to the diaphragm and a correction coefficient for the lower cardiac portion relative to the diaphragm, and calculates the average value of the correction coefficients as a correction coefficient for the overall heart. It is, however, possible to selectively use one of the correction coefficients for the upper cardiac portion and the lower cardiac portion in accordance with a target portion of the heart. It is also possible to obtain a correction coefficient for each frame and selectively use any of the correction coefficients in accordance with the moving amount of the diaphragm detected by a navigate scan of a main scan. In addition, it is possible to obtain correction coefficients for an expiratory period and an inspiratory period and selectively use the correction coefficients in an expiratory period and an inspiratory period. These operations will be described in detail later as modifications of the embodiment.

In addition, it is possible to distribute the moving amounts of the diaphragm and the moving amounts of the heart obtained from the respective frames on the abscissa and ordinate respectively representing the moving amounts of the diaphragm and the moving amounts of the heart, linearly approximate the resultant moving amount distributions, and obtain their gradients as correction coefficients. Furthermore, it is possible to use a statistical technique such as the least squares method. In this case, for example, it is possible to obtain a correction coefficient by calculating the differences between the moving amounts of the diaphragm and the moving amounts of the heart by which coefficients are multiplied for the respective frames, calculating the sums of squares, and searching for a correlation corresponding to the minimum sum of squares.

Figure 5:
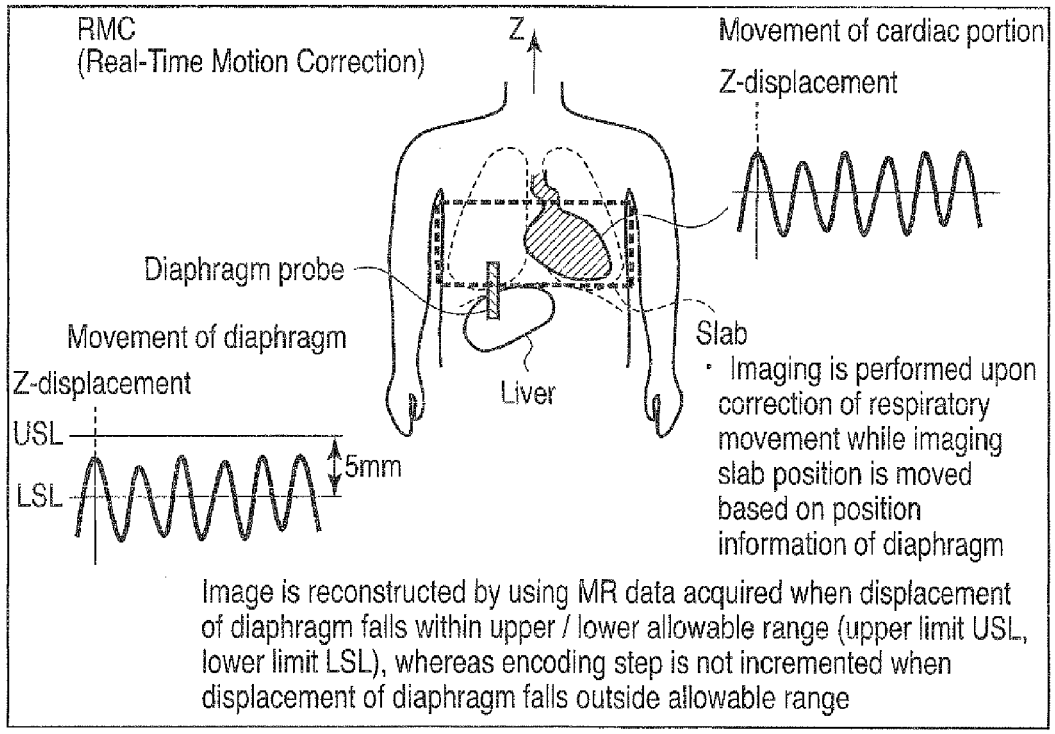
FIG. 5 is a view for explaining how the correction coefficient obtained by the preliminary scanning in FIG. 2 is applied to main scanning (RMC (Real-time Motion Correction))
Figure 6:
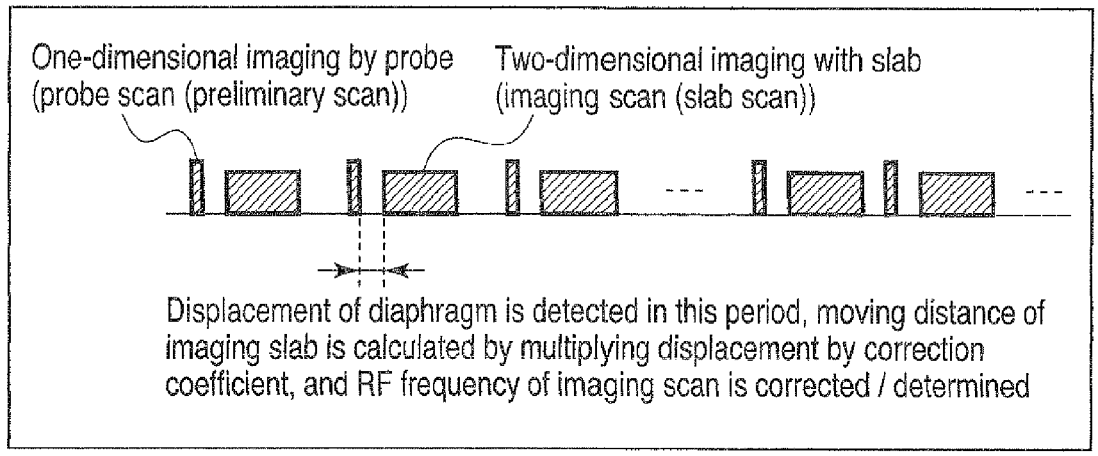
FIG. 6 is a view for explaining main scanning in FIG. 5.

After correction coefficients are obtained in this manner, a WHMR imaging control unit 10p executes a main scan by controlling the transmission unit 7, the reception unit 9, and the gradient field power supply 3. As shown in FIGS. 5 and 6, a main scan is performed by using a technique called RMC (Real-time Motion Correction) to suitably image the overall heart of the object while tracking the heart which moves due to the respiratory movement of the object. In this operation, the apparatus repeats an imaging scan (slab scan) for imaging a slab including the overall heart accompanying phase-encode increment using a two- or three-dimensional Fourier transform method. Immediately before each imaging scan, the apparatus executes a probe scan (navigator scan) for detecting the moving distance, i.e., the moving amount, of the diaphragm, which moves due to the respiratory movement of the object, from a reference position (the position in the first scan).

A diaphragm displacement detection unit 10m detects the moving amount of the diaphragm from a reference position in the initial frame in a main scan from one- or two-dimensional image associated with the diaphragm detected by a navigator scan. As shown in FIG. 5, a vertical movement allowance determination unit 10n determines whether the moving amount of the diaphragm detected by the diaphragm displacement detection unit 10m falls within, for example, the allowable range of 5 mm between an upper limit USL and a lower limit LSL which are set in advance. If the moving amount of the diaphragm falls outside the allowable range, the WHMR imaging control unit 10p executes an imaging scan but does not increment phase encoding value. The WHMR imaging control unit lop gives the same phase encoding value to an MR signal in the next imaging scan. That is, MR data obtained when the moving amount of the diaphragm falls outside the allowable range is excluded from image reconstruction. This will reduce motion artifacts.

A slab displacement calculation unit 10q multiplies the moving amount of the diaphragm detected by the diaphragm displacement detection unit 10m in the interval between a navigator scan and an immediately succeeding imaging scan by the correction coefficient calculated by a preliminary scan. The WHMR imaging control unit lop shifts the center frequency of a transmission RP pulse to move the imaging slab (excitation range) by the calculated slab moving amount, and then executes an immediately succeeding imaging scan. The WHMR imaging control unit 10p acquires MR data having all phase encoding values necessary for image reconstruction while alternately repeating a navigator scan and an imaging scan in this manner.

As described above, this embodiment allows one to easily obtain a correction coefficient used for WHMRCA imaging immediately before imaging even if the object changes to another object. Performing WHMRCA imaging using this correction coefficient can perform high image quality WHMRCA imaging more reliably without fail.

Figure 7:
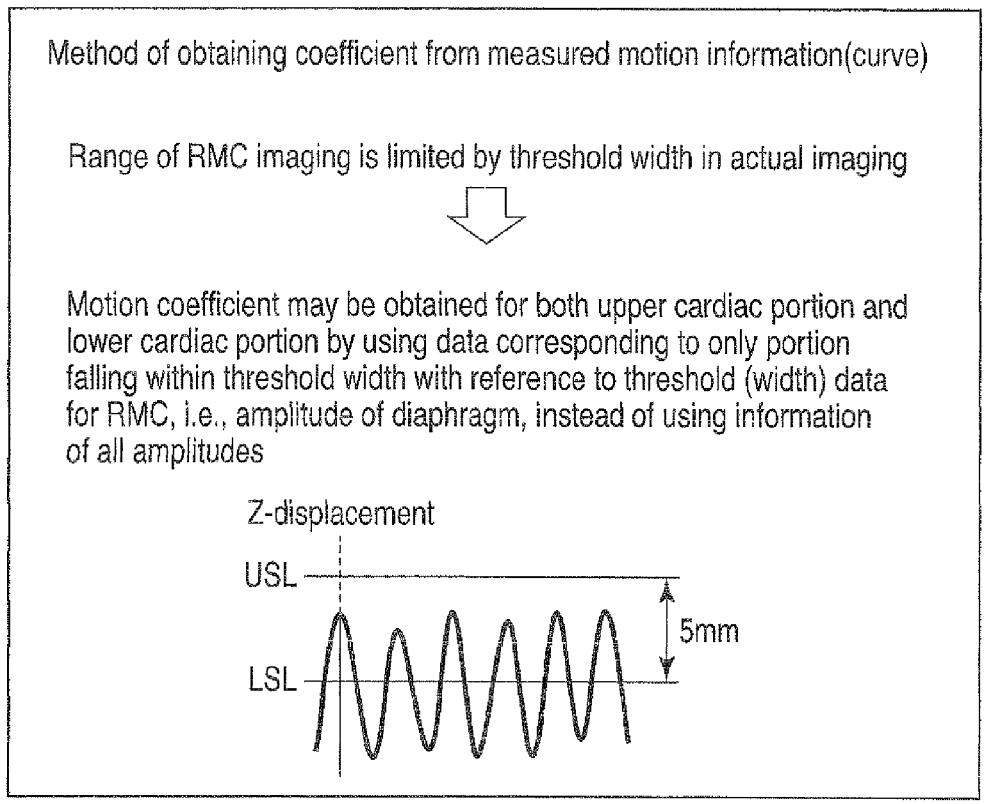
FIG. 7 is a view for explaining the first modification of this embodiment.

FIG. 7 shows the first modification of this embodiment. As described above, although a correction coefficient is calculated by obtaining an average moving amount concerning all the frames, an actual scan is performed to acquire effective data used for image reconstruction by incrementing the phase encoding value when the moving amount of the diaphragm falls within the allowable range, as shown in FIG. 5. As shown in FIG. 7, therefore, it is possible to calculate a correction coefficient by using only the moving amounts of the diaphragm and heart concerning only frames when the moving amount of the diaphragm falls within the allowable range.

Figure 8:
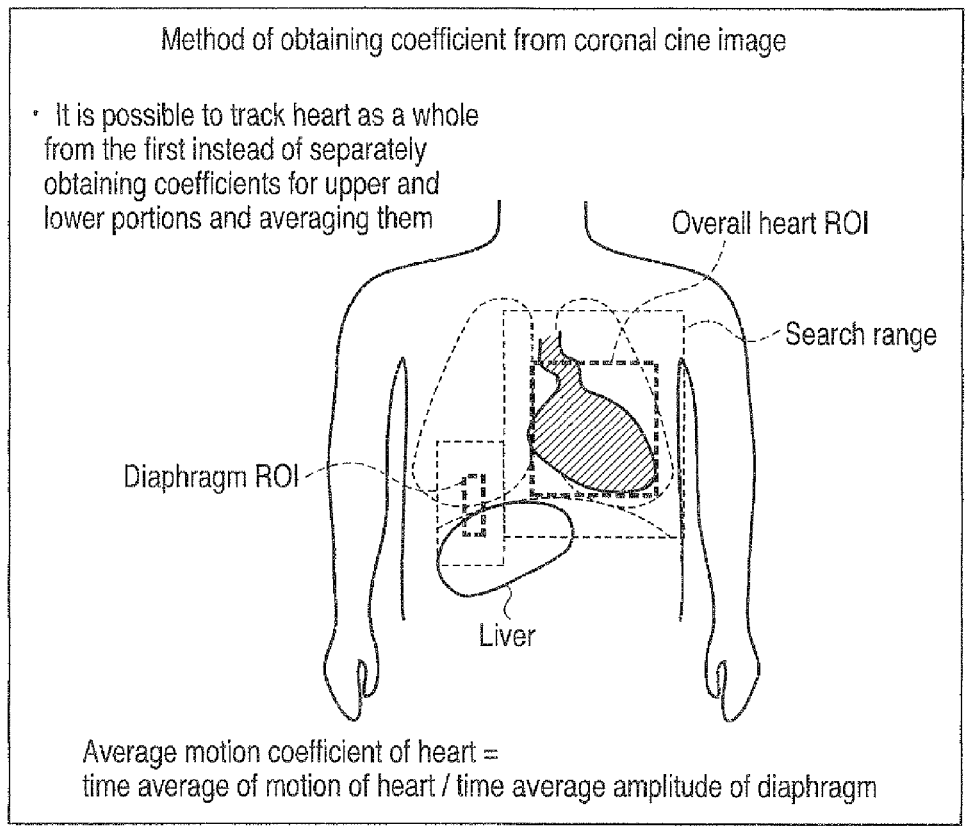
FIG. 8 is a view for explaining the second modification of this embodiment.

FIG. 8 shows the second modification of this embodiment. The embodiment described above sets ROIs at the upper and lower portions of the heart in addition to a diaphragm ROI, obtains correction coefficients separately for the respective ROIs, and then calculates an average as a correction coefficient. As shown in FIG. 8, it is possible to set a relatively large single ROI including almost the entire heart for the heart and perform pattern matching to obtain temporal changes in the moving amount of the overall heart. In this case, the motion coefficient of the overall heart is given by correction coefficient of overall heart=average value of temporal changes in moving amount of overall heart/average value of temporal changes in moving amount of diaphragm.

Figure 9:
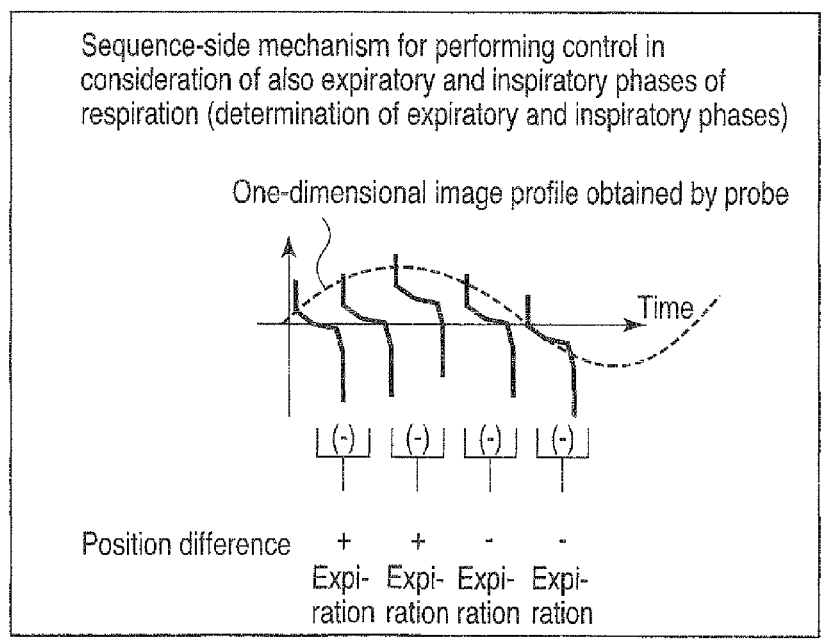
FIG. 9 is a view for explaining the third modification of this embodiment.

The third modification of this embodiment will be described next. The embodiment described above gives no consideration to the difference between the expiratory and inspiratory phases of a respiration. It is, however, possible to separately obtain a correction coefficient corresponding to an expiratory phase and an correction coefficient corresponding to an inspiratory phase while giving consideration to the expiratory and inspiratory phases of a respiration upon analysis on coronal dine images. When performing main scanning/imaging, the apparatus selectively uses correction coefficients depending on an expiratory phase and an inspiratory phase by using correction coefficients corresponding to an expiratory phase and an inspiratory phase. More specifically, the apparatus obtains an array of correction coefficients on a respiratory position basis for each respiratory phase position in advance, and performs imaging upon correction while changing a correction coefficient at each time point in an entire respiratory phase. This operation requires a mechanism of discriminating an expiratory phase from an inspiratory phase. For this reason, for example, as shown in FIG. 9, the vertical movement allowance determination unit ion obtains differences between motion probe signal waveforms in the time direction, and performs correction while changing correction coefficients so as to use a correction coefficient corresponding to an expiratory phase when the position change is positive, and a correction coefficient corresponding to an inspiratory phase when the position change is negative. At this time, the smaller the number of probe signals to be sampled, the larger the number of determination errors, and hence it is preferable to improve the accuracy by performing multi-probe operation or the like.

Figure 10:
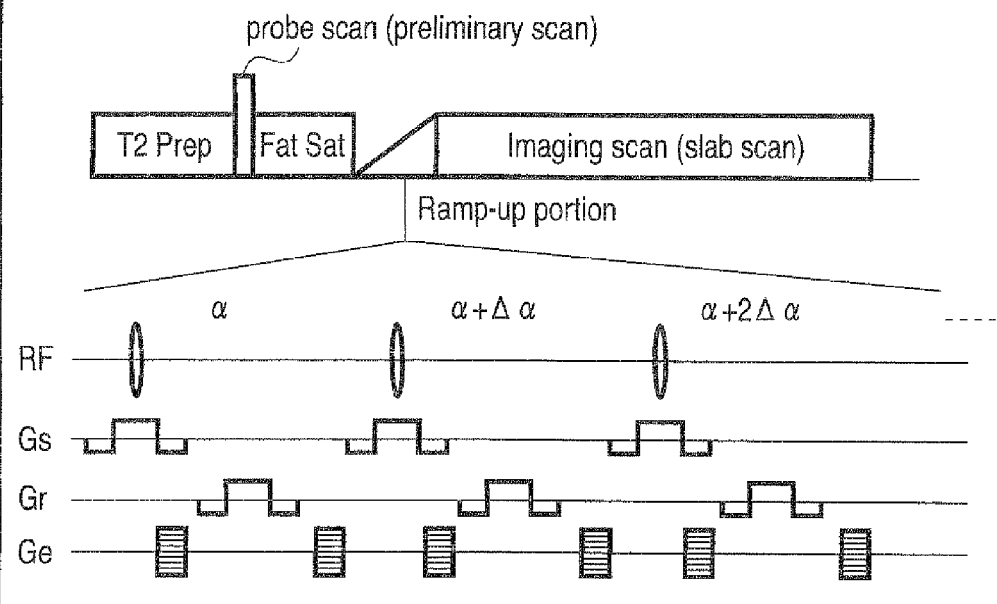
FIG. 10 is a view for explaining the fourth modification of this embodiment.
Figure 11:
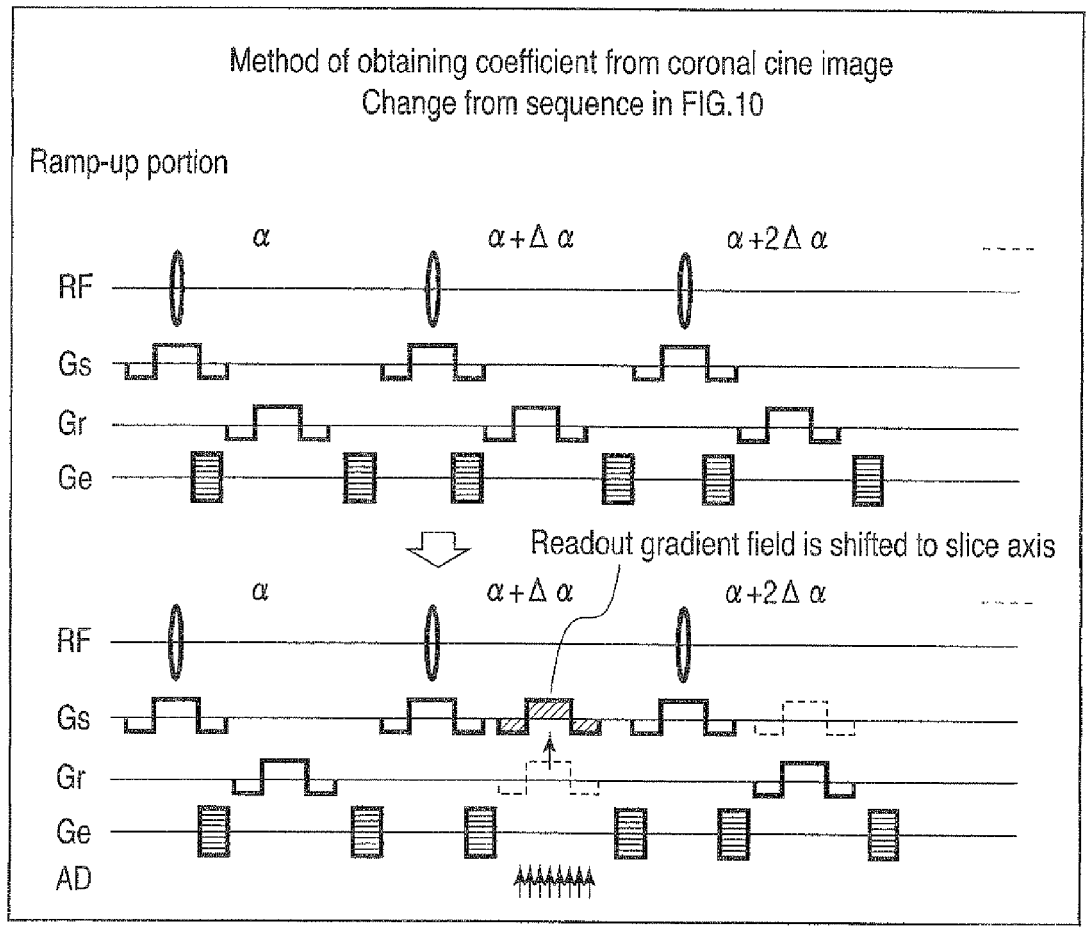
FIG. 11 is a view showing a pulse sequence in a ramp-up portion in FIG. 10.
Figure 12:
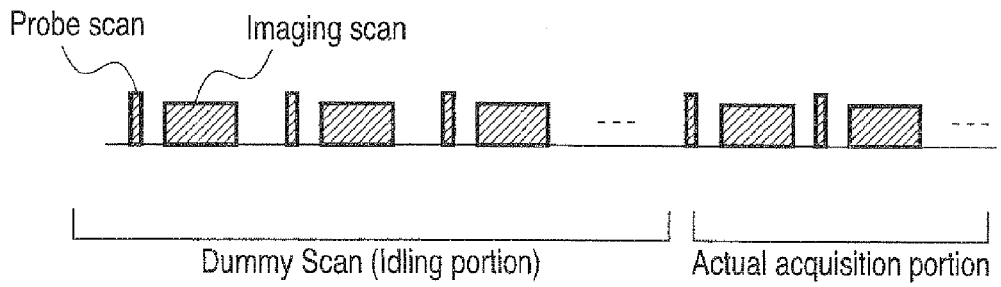
FIG. 12 is a view for explaining a protocol before scanning and a scan start timing in the fourth modification of this embodiment.

FIG. 10 shows the fourth modification of this embodiment. This modification is a method of acquiring a correction coefficient during a sequence for a main scan by using the ramp-up portion between a navigator scan (motion probe) and an imaging scan in the main scan, instead of obtaining a correction coefficient by using coronal cine images captured in advance. As shown in FIG. 10, a ramp-up portion in the sequence is used. FIG. 11 shows a pulse sequence corresponding to the ramp-up portion. In at least one block of the RF application blocks repeated in the ramp-up portion, the apparatus acquires data by performing ADC sampling upon moving the readout gradient field, which is generally applied in the read direction, to the slice axis. FIG. 12 further shows procedures concerning a protocol before a san and a scan starting method which are associated with this method. The apparatus obtains coefficients concerning an idling portion and an actual data acquisition portion by the following procedure and method, and uses the coefficients for imaging.

1) When acquiring actual data, the apparatus stores a moving amount signal in the slice direction in a start-up portion in advance. When performing image reconstruction after a scan, the apparatus reconstructs an image upon restoring only a moving amount component. That is, the apparatus applies a phase change corresponding to the moving amount to all data.

2) In an idling portion, a motion probe signal is compared with moving amount information in a start-up portion. This can obtain a more accurate motion coefficient. When starting actual acquisition, the apparatus acquires data upon replacing the motion coefficient in the sequence with this coefficient with higher accuracy.

3) Using the above mechanism can obtain the motion phase difference between the diaphragm and the heart (the phase difference between the motion of the diaphragm and the motion of the heart) and the like in advance. The apparatus performs WHMRCA imaging while performing correction in consideration of also the phase difference by using this information.

4) In this case, increasing the number of times repeating an idling period (during which motion information is acquired) before actual data acquisition (to, for example, about 20 to 30) makes it possible to expect a further improvement in accuracy.

These methods allow one to obtain motion coefficients concerning the diaphragm and the heart in advance without capturing coronal cine images in advance. This makes it possible to implement high image quality visualization in a shorter period of time.

The present invention can be further variously modified. It is possible to set the encode for actual data acquisition to 0 only in an idling period instead of applying a change to the ramp-up portion of a sequence in the above case, acquire motion information using the corresponding data, obtain more accurate motion information from a motion coefficient relative to the motion probe portion, and perform imaging upon correction. In addition, it is possible to prepare several motion models by using an idling period, determine parameters for the models, and use them for actual imaging operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   an assembly of MRI components including static and gradient magnetic field generators and at least one radio frequency (RF) coil defining an imaging volume;
   a computer system, connected to control said assembly of components, including at least one RF transmitter and at least one RF receiver, said computer system being configured to effect MRI scans including specified MRI data acquisition sequences of RF and gradient magnetic field pulses which produce nuclear magnetic resonance (NMR) spin responses emanating from different spatially located volumes of NMR nuclei as a function of a magnetic field experienced by the nuclei;
   said computer system being configured to control said assembly of MRI components to:
   repeat plural MRI scans on a heart of an object,
   detect a moving amount of a diaphragm due to respiratory movement of the object by executing a probe scan immediately before each of the MRI scans, and
   move an imaging range for each of the MRI scans based, in part, on the detected moving amount of the diaphragm by
      repeatedly capturing data of at least one image associated with at least one slice including the heart and the diaphragm using ECG gating as a preliminary scan for the probe scan and the MRI scan;
      generating a temporal change in the detected moving amount of the diaphragm and a temporal change in the detected moving amount of the heart from the repeatedly captured images;
      calculating a ratio of the detected moving amount of the heart to the detected moving amount of the diaphragm based on the generated temporal change in the detected moving amount of the diaphragm and the generated temporal change in the detected moving amount of the heart; and
      calculating a moving amount for an imaging range used in each of the MRI scans, after correcting the moving amount of the diaphragm detected by each of the probe scans, based on the calculated ratio.

2. The apparatus according to claim 1, wherein a coronal image associated with a slice traversing the diaphragm and overall heart of the object is captured.

3. The apparatus according to claim 1, wherein a plurality of coronal images associated with a plurality of slices is captured.

4. The apparatus according to claim 1, wherein the following images are captured:
   a coronal image associated with a slice traversing the diaphragm of the object,
   a coronal image associated with a slice traversing an upper cardiac portion of the object, and
   a coronal image associated with a slice traversing a lower cardiac portion of the object.

5. The apparatus according to claim 1, wherein the data for at least one image is captured by using an SSFP (steady state free precession) imaging method.

6. The apparatus according to claim 1, wherein the data for at least one image is captured in synchronism with a diastolic phase of the heart.

7. The apparatus according to claim 1, wherein the computer control circuits are also programmed to specify, in the repeatedly captured images, a temporal change in a moving amount of the diaphragm by searching for a position in each frame which exhibits a highest correlation with reference to an image pattern of a local region traversing the diaphragm in an initial frame.

8. The apparatus according to claim 7, wherein the local region comprises a two-dimensional region.

9. The apparatus according to claim 7, wherein the computer system is configured to generate for the repeatedly captured images a temporal change in a moving amount of the heart by searching for a position in each frame which exhibits a highest correlation with reference to an image pattern of a local region traversing a boundary edge portion of the heart in an initial frame.

10. The apparatus according to claim 7, wherein the computer system is configured to generate for the repeatedly captured images:
    a temporal change in a moving amount of an upper portion of the heart by searching for a position in each frame which exhibits a highest correlation with reference to image patterns of a plurality of local regions traversing a boundary edge portion of the upper portion of the heart in an initial frame,
    a temporal change in a moving amount of a lower portion of the heart by searching for a position in each frame which exhibits a highest correlation with reference to image patterns of a plurality of local regions traversing a boundary edge portion of the lower portion of the heart in the initial frame, and
    a temporal change in a moving amount of the heart based on the temporal change in a moving amount of the upper portion of the heart and the temporal change in a moving amount of the lower portion of the heart.

11. The apparatus according to claim 1, wherein the computer system is configured to calculate:
    a time average of moving amounts of the diaphragm from the temporal change in moving amount of the diaphragm,
    a time average associated with the heart from the temporal change in moving amount of the heart, and
    a ratio of the time average associated with the heart to the time average associated with the diaphragm.

12. The apparatus according to claim 10, wherein the computer system is configured to calculate:
    a time average of moving amounts of the diaphragm from the temporal change in moving amount of the diaphragm,
    a time average of moving amounts of the upper portion of the heart from the temporal change in moving amount of the upper portion of the heart,
    a time average of moving amounts of the lower portion of the heart from the temporal change in moving amount of the lower portion of the heart,
    an upper portion ratio of the time average associated with the upper portion of the heart to the time average associated with the diaphragm,
    a lower portion ratio of the time average associated with the lower portion of the heart to the time average associated with the diaphragm, and
    an average ratio of the upper portion ratio and lower portion ratio as a ratio of the moving amount of the heart to the moving amount of the diaphragm.

13. The apparatus according to claim 10, wherein the computer system is configured to calculate:
    a time average of moving amounts of the diaphragm from the temporal change in moving amount of the diaphragm, a time average of moving amounts of the upper portion of the heart from the temporal change in moving amount of the upper portion of the heart, a time average of moving amounts of the lower portion of the heart from the temporal change in moving amount of the lower portion of the heart, an upper portion ratio of the time average associated with the upper portion of the heart to the time average associated with the diaphragm, a lower portion ratio of the time average associated with the lower portion of the heart to the time average associated with the diaphragm, and a weighted average of the upper portion ratio and lower portion ratio which is calculated as a ratio of the moving amount of the heart to the moving amount of the diaphragm.

14. The apparatus according to claim 10, wherein the computer system is configured to:

reconstruct an image based on MR data acquired by the imaging scan when the detected moving amount of the diaphragm falls within a predetermined range, and calculate a ratio of the moving amount of the heart to the moving amount of the diaphragm only within the predetermined range.

15. The apparatus according to claim 7, wherein the computer system is configured to generate for the repeatedly captured images, a temporal change in a moving amount of the heart specified by searching for a position in each frame which exhibits a highest correlation with reference to an image pattern of a local region including a majority of the heart in an initial frame.

16. The apparatus according to claim 1, wherein the computer system is also configured to calculate a ratio of the moving amount of the heart to the moving amount of the diaphragm based on an expiratory phase and inspiratory phase of the object.

17. A magnetic resonance imaging (MRI) apparatus comprising:

an assembly of MRI components including static and gradient magnetic field generators and at least one radio frequency (RF) coil defining an imaging volume;

a computer system, connected to control said assembly of components, including at least one RF transmitter and at least one RF receiver to effect MRI scans including specified MRI data acquisition sequences of RF and gradient magnetic field pulses which produce nuclear magnetic resonance (NMR) spin responses emanating from different spatially located volumes of NMR nuclei as a function of a magnetic field experienced by the nuclei;

said computer system being configured to repeatedly:

execute an MRI scan on a heart of an object, execute a probe scan to detect a moving amount of a diaphragm due to respiratory movement of the object immediately before each of the MRI scans, and execute a ramp-up scan for imaging a partial region of the heart of the object between the probe scan and the MRI scan by generating a temporal change in a moving amount of the diaphragm from images of the diaphragm repeatedly captured by the probe scans;

generating a temporal change in a moving amount of the partial region of the heart repeatedly imaged by the ramp-up scans;

calculating a ratio of a moving amount of the heart to a moving amount of the diaphragm; and calculating a moving amount for an imaging range used in each of the MRI scans by correcting the moving amount of the diaphragm detected by each of the probe scans based on the calculated ratio.

18. A magnetic resonance imaging apparatus comprising:

an assembly of MRI components including static and gradient magnetic field generators and at least one radio frequency (RF) coil defining an imaging volume;

a computer system, connected to control said assembly of components, including at least one RF transmitter and at least one RF receiver, said computer system being configured to effect MRI scans including specified MRI data acquisition sequences of RF and gradient magnetic field pulses which produce nuclear magnetic resonance (NMR) spin responses emanating from different spatially located volumes of NMR nuclei as a function of a magnetic field experienced by the nuclei;

said computer system being configured to:

repeat plural MRI scans on a heart of an object, detect a moving amount of a diaphragm of the object by executing a probe scan immediately before each of the MRI scans, and move an imaging range for each of the MRI scans based, in part, on the detected moving amount of the diaphragm by calculating a ratio of the moving amount of the heart to the moving amount of the diaphragm from images captured in advance by the probe scans and the MRI scans; and setting a position of an imaging range used in each of the MRI scans based on the detected moving amount of the diaphragm by the respectively associated probe scan and the calculated ratio.

19. An image processing apparatus comprising:

a computer system configured to access digital data defining a series of successively acquired plural images associated with an imaging range including a heart and a diaphragm of an object;

generate a temporal change in a moving amount of the diaphragm and a temporal change in a moving amount of the heart from the series of images;

calculate a ratio of the moving amount of the heart to the moving amount of the diaphragm based on a ratio of the generated temporal changes in moving amounts of the heart and diaphragm, use the calculated ratio to correct accessed images of the heart for movements of the heart over plural successively acquired images of the heart; and display a resulting motion-corrected image of the heart.

* * * * *